(12) United States Patent
Liu

(10) Patent No.: US 11,779,056 B2
(45) Date of Patent: Oct. 10, 2023

(54) ATOMIZER

(71) Applicant: SHENZHEN BUDDY TECHNOLOGY DEVELOPMENT CO., LTD., Shenzhen (CN)

(72) Inventor: Xiang Liu, Shenzhen (CN)

(73) Assignee: SHENZHEN BUDDY TECHNOLOGY DEVELOPMENT CO., LTD., Shenzhen (CN)

( * ) Notice: Subject to any disclaimer, the term of this patent is extended or adjusted under 35 U.S.C. 154(b) by 545 days.

(21) Appl. No.: 17/012,364

(22) Filed: Sep. 4, 2020

(65) Prior Publication Data

US 2022/0015456 A1 Jan. 20, 2022

(30) Foreign Application Priority Data

Jul. 15, 2020 (CN) .......................... 202021390533.2

(51) Int. Cl.
*A24F 40/95* (2020.01)
*A61M 15/00* (2006.01)
(Continued)

(52) U.S. Cl.
CPC .............. *A24F 40/95* (2020.01); *A24F 40/46* (2020.01); *A24F 40/53* (2020.01);
(Continued)

(58) Field of Classification Search
CPC .......... A61M 2205/8206; A61M 15/00; A61M 15/0086; A61M 2205/8237;
(Continued)

(56) References Cited

U.S. PATENT DOCUMENTS

| 2013/0152922 A1* | 6/2013 | Benassayag | ......... A61M 11/042 128/202.21 |
| 2014/0311503 A1* | 10/2014 | Liu | .......................... A24F 40/00 131/329 |

(Continued)

*Primary Examiner* — Samchuan C Yao
*Assistant Examiner* — Yurie Hong
(74) *Attorney, Agent, or Firm* — WPAT, P.C

(57) ABSTRACT

An atomizer is provided. The atomizer includes a battery rod, including a rod body, a battery, and a first electrical connection part arranged on the rod body and exposed from the rod body, wherein an end of the rod body is disposed with a receiving part, and the first electrical connection part is located in the receiving part, an atomizing head, including a housing and a second electrical connection part arranged on the housing and exposed from the housing, and a mechanical switch, arranged on the rod body and exposed outside the rod body, wherein the mechanical switch is electrically connected between the battery and the first electrical connection part, and configured to turn on or turn off an electrical connection between the battery and the first electrical connection part; wherein the first electrical connection part is in contact with the second electrical connection part when the atomizing head is inserted into the receiving part, the electrical connection between the battery and the first electrical connection part is turned on when the atomizing head is inserted into the receiving part and the mechanical switch is triggered, and thereby an electrical connection between the first electrical connection part and the second electrical connection part is turned on to supply a power to the atomizing head through the battery. Using the mechanical switch to control the battery rod whether supply a power to the atomizing head or not can ensure the effectiveness of triggering power supply for a long time.

20 Claims, 5 Drawing Sheets

(51) Int. Cl.
*A24F 40/46* (2020.01)
*A24F 40/53* (2020.01)

(52) U.S. Cl.
CPC .... *A61M 15/0001* (2014.02); *A61M 15/0086* (2013.01); *A61M 2205/8206* (2013.01); *A61M 2205/8237* (2013.01)

(58) Field of Classification Search
CPC ..... A61M 15/0001; A24F 40/10; A24F 40/40; A24F 40/90
See application file for complete search history.

(56) References Cited

U.S. PATENT DOCUMENTS

| | | | | |
|---|---|---|---|---|
| 2014/0360516 | A1* | 12/2014 | Liu | A61M 15/06 131/329 |
| 2015/0059782 | A1* | 3/2015 | Liu | A24F 40/50 131/329 |
| 2015/0128976 | A1* | 5/2015 | Verleur | H02J 7/00 131/329 |
| 2016/0286860 | A1* | 10/2016 | Flayler | A61M 11/042 |
| 2016/0331033 | A1* | 11/2016 | Hopps | H05B 1/0227 |
| 2016/0345627 | A1* | 12/2016 | Liu | A24F 40/95 |
| 2017/0150756 | A1* | 6/2017 | Rexroad | H05B 1/0244 |

* cited by examiner

ATOMIZER

TECHNICAL FIELD

The disclosure relates to the field of appliances technologies, and more particularly to an atomizer.

DESCRIPTION OF RELATED ART

At present, a power supply of an atomizer is triggered by a diaphragm microphone. The diaphragm microphone is an airflow sensing switch. Its working principle is that: when an airflow through the diaphragm microphone, a pressure difference is formed between a front side and a back side of the diaphragm microphone, at this time, a circuit between a control battery and the atomizer is turned on and a battery supplies power to the atomizer consequently. However, the diaphragm microphone cannot work due to being soaked by condensate, resulting in the failure to trigger the supply of the power.

SUMMARY

In view of the above issues, embodiments of the disclosure provide an atomizer.

An embodiment of the disclosure provides an atomizer, the atomizer includes:

a battery rod, including a rod body, a battery contained in the rod body, and a first electrical connection part arranged on the rod body and exposed from the rod body, an end of the rod body is disposed with a receiving part, and the first electrical connection part is located in the receiving part;

an atomizing head, including a housing and a second electrical connection part arranged on the housing and exposed from the housing;

a mechanical switch, arranged on the rod body and exposed outside the rod body, the mechanical switch is electrically connected between the battery and the first electrical connection part, and configured to turn on or turn off an electrical connection between the battery and the first electrical connection part;

the first electrical connection part is in contact with the second electrical connection part when the atomizing head is inserted into the receiving part;

the electrical connection between the battery and the first electrical connection part is turned on when the atomizing head is inserted into the receiving part and the mechanical switch is triggered, and thereby an electrical connection between the first electrical connection part and the second electrical connection part is turned on to supply a power to the atomizing head through the battery.

In an embodiment, the battery rod also includes a main control board, a switch board and a control circuit; the main control board, the switch board and the control circuit are all contained in the rod body;

the switch board includes a touch control part, and the mechanical switch is cooperative with the touch control part; the switch board is configured to obtain a trigger information of the mechanical switch, and the trigger information comprises a first duration of the mechanical switch being triggered and/or a number of times of the mechanical switch being triggered in a preset time period;

the first electrical connection part is electrically connected with the control circuit;

the main control board is electrically connected with the battery, the switch board and the control circuit individually, the main control board is capable of controlling the battery rod to be turned on or be turned off according to the trigger information; and after the battery rod is turned on, the main control board is capable of controlling the control circuit to whether output a current to the first electrical connection part or not according to the trigger information, and a magnitude and/or a second duration of the current outputted from the control circuit, and is further capable of controlling a voltage output rank of the atomizer.

In an embodiment, the mechanical switch includes an operation part and a connection part, the connection part is arranged on a side of the operation part, the connection part is matched with the touch control part in a concave-convex manner, a part of the operation part is exposed outside the housing, and the connection part is a flexible structure; and/or, at least two of the main control board, the switch board and the control circuit are integrated into one piece.

In an embodiment, the battery rod further comprises a charging interface arranged on the rod body and exposed outside the rod body, the charging interface is electrically connected with the main control board, and the charging interface is configured to connect with an external power source;

the main control board controls the external power source to charge the battery when the charging interface is connected with the external power source.

In an embodiment, the battery rod also includes an indicator light electrically connected with the main control board, and the main control board is configured to control a display of the indicator light according to the trigger information.

In an embodiment, the indicator light includes at least one of a rank indicator light, a battery's power indicator light, a charging indicator light and an abnormal status indicator light; and/or, the battery rod also includes a shading structure, and a light emitted from the indicator light is directed outside the rod body after passing through the shading structure; and/or, the shading structure is a flexible structure.

In an embodiment, the first electrical connection part is one of an electric pin and an electric socket, and the second electrical connection part is the other of the electric pin and the electric socket; and/or, the first electrical connection part includes two electric pins, and the second electrical connection part includes two electric sockets, and the two electric pins are matched with the two electric sockets.

In an embodiment, the battery rod also includes first magnetic parts arranged on the rod body and on two sides of the first electrical connection part, and the first magnetic parts are located in the receiving part;

the atomizing head also includes second magnetic parts arranged on the housing and on two sides of the second electrical connection part;

the first magnetic parts are magnetically connected with the second magnetic parts to fix the atomizing head on the battery rod when the atomizing head is inserted into the receiving part.

In an embodiment, the atomizing head also includes a material-receiving cup contained in the housing and an atomizing nozzle sleeved on the housing and exposed outside;

a gap is arranged to a top of the material-receiving cup, and the gap is sealed by a sealing plug;

an needle located outside of the atomizer passes through the sealing plug from the atomizing nozzle and enters into the material-receiving cup to inject materials when the atomizing head is inverted;

the sealing plug is restored automatically under an action of a surrounding pressure to seal the gap after the needle is pulled out.

In an embodiment, the atomizing head also includes a heating element, the heating element is arranged under the material-receiving cup, and the heating element is made of a ceramic material; and/or, the heating element is an interior-type lead-free ceramic heater (also referred to as buried lead-free ceramic heater).

The above technical solutions may have one or more of the following advantages or benefits: the mechanical switch is used to control the battery rod whether supply a power to the atomizing head or not and the mechanical switch has a long life to thereby ensure the effectiveness of triggering power supply for a long time.

BRIEF DESCRIPTION OF THE DRAWINGS

In order to more clearly illustrate technical solutions of embodiments of the disclosure, drawings used in the description of the embodiments will be briefly described below. Apparently, the drawings described below are merely some embodiments of the disclosure, and those skilled in the art can obtain other drawings based on these drawings without creative efforts.

FIGURE REFERENCE NUMBERS

Figure 1:
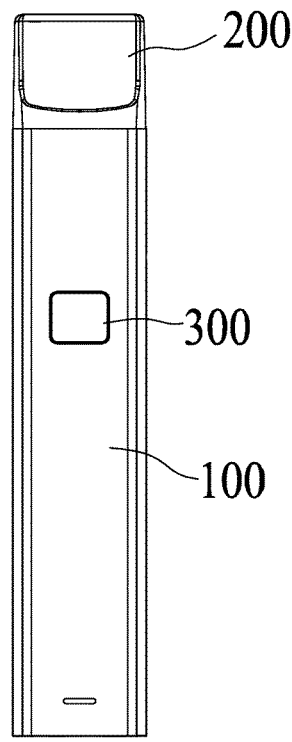
FIG. 1 is a schematic isometric view of an atomizer in a use state according to an embodiment of the disclosure.
Figure 2:
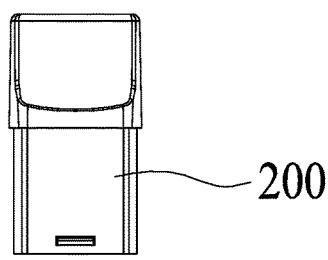
FIG. 2 is a schematic disassembled structural view of the atomizer according to an embodiment of the disclosure.
Figure 2:
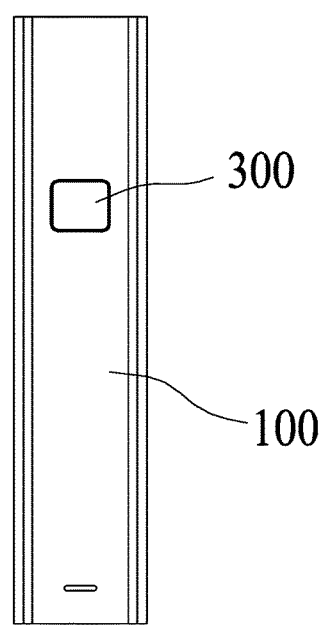
Figure 3:
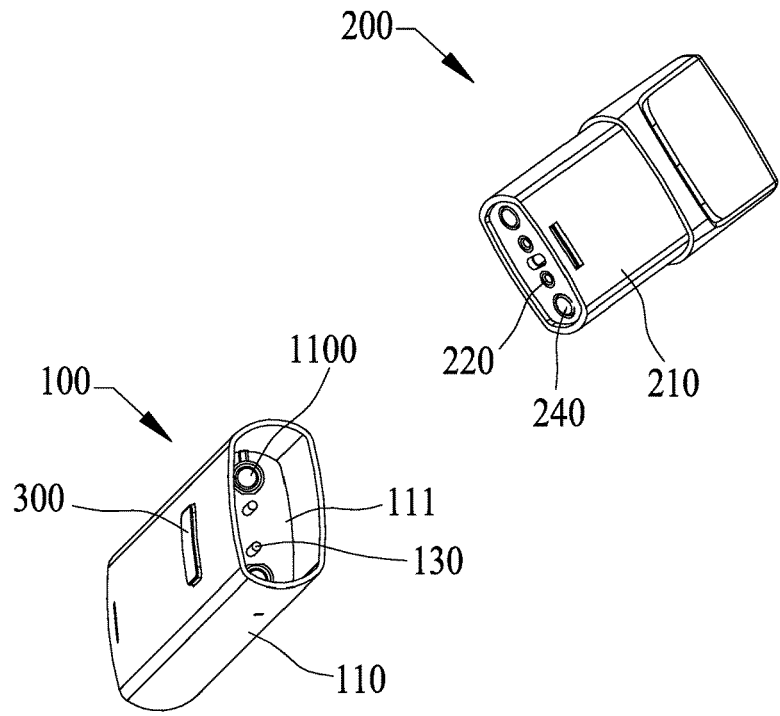
FIG. 3 is a schematic disassembled perspective view of the atomizer observed in another direction according to an embodiment of the disclosure.

100: battery rod; 110: rod body; 111: receiving part; 120: battery; 130: first electrical connection part; 140: main control board; 150: switch board; 151: touch control part; 160: control circuit; 170: mainboard bracket; 180: indicator light; 181: rank indicator light; 182: battery's power indicator light; 183: charging indicator light; 184: abnormal status indicator light; 190: shading structure; 1100: first magnetic parts; 1200: flexible sheath;

200: atomizing head; 210: housing; 220: second electrical connection part; 230: first block; 240: second magnetic parts; 250: material-receiving cup; 260: atomizing nozzle; 270: sealing plug; 280: heating element; 290: second block; 2100: flexible part; 2200: first flexible ring; 2300: second flexible ring;

300: mechanical switch; 310: operation part; 320: connection part;

400: needle.

DETAILED DESCRIPTION OF EMBODIMENTS

The technical solutions in the embodiments of the disclosure will be clearly and completely described below, with reference to the accompanying drawings in the embodiments of the disclosure. Apparently, the described embodiments are merely some of the embodiments of the disclosure, not all embodiments. Based on the described embodiments of the disclosure, all the other embodiments obtained by those skilled in the art without any creativity should belong to the protective scope of the disclosure.

It should be noted that the terms "first" and "second" in the description and claims of the disclosure and the above drawings are used to distinguish similar objects, and do not have to be used to describe a specific order or sequence. It should be understood that the terms so used are interchangeable under appropriate circumstances so that the embodiments of the disclosure described herein can be implemented in an order other than those illustrated or described herein. In addition, the terms "including" and "having" and any variations thereof are intended to cover non-exclusive inclusions, for example, processes, methods, systems, products or devices that contain a series of steps or units need not be limited to those clearly listed those steps or units, but may include other steps or units not explicitly listed or inherent to these processes, methods, products or equipment.

As shown in FIGS. 1 to 5, an embodiment of the disclosure provides an atomizer, the atomizer includes a battery rod 100, an atomizing head 200 and a mechanical switch 300, in an exemplary embodiment, the battery rod 100 includes a rod body 110, a battery 120 contained in the rod body 110, and a first electrical connection part 130 arranged on the rod body 110 and exposed from the rod body 110. In the embodiment, an end of the rod body 110 is disposed with a receiving part 111, and the first electrical connection part 130 is located in the receiving part 111. The receiving part 111 is used for inserting the atomizing head 200 so that the atomizing head 200 are matched with the battery rod 100, that is, the atomizing head 200 can be detachably mounted on the battery rod 100. The atomizing head 200 includes a housing 210 and a second electrical connection part 220 arranged on the housing 210 and exposed from the housing 210. Further, the mechanical switch 300 is arranged on the rod body 110 and exposed outside the rod body 110. In the embodiment, the mechanical switch 300 is electrically connected between the battery 120 and the first electrical connection part 130, and the mechanical switch is configured to turn on or turn off an electrical connection between the battery 120 and the first electrical connection part 130.

In an embodiment of the disclosure, the first electrical connection part 130 is in contact with the second electrical connection part 220 when the atomizing head 200 is inserted into the receiving part 111, in other words, when the atomizing head 200 is cooperative with the battery rod 100, the first electrical connection part 130 is in contact with the second electrical connection part 220.

The electrical connection between the battery 120 and the first electrical connection part 130 is turned on when the atomizing head 200 is inserted into the receiving part 111 and the mechanical switch 300 is triggered, and thereby an electrical connection between the first electrical connection part 130 and the second electrical connection part 220 is turned on to supply a power to the atomizing head 200 through the battery 120. It should be noted that the mechanical switch 300 is triggered means that the mechanical switch 300 is operated, for example, the mechanical switch 300 can be operated by a user. In an embodiment of the disclosure, the mechanical switch 300 is used to control the battery rod 100 whether supply the power to the atomizing head 200 or not, and the mechanical switch 300 has a long life to thereby ensure the effectiveness of triggering power supply for a long time.

The mechanical switch 300 is operated by the user is related to a structure of the mechanical switch 300, when the mechanical switch 300 is a push switch, the user presses the mechanical switch 300 to trigger the mechanical switch 300; when the mechanical switch 300 is a rotary switch, the user rotates the mechanical switch 300 to trigger the mechanical switch 300.

Figure 4:
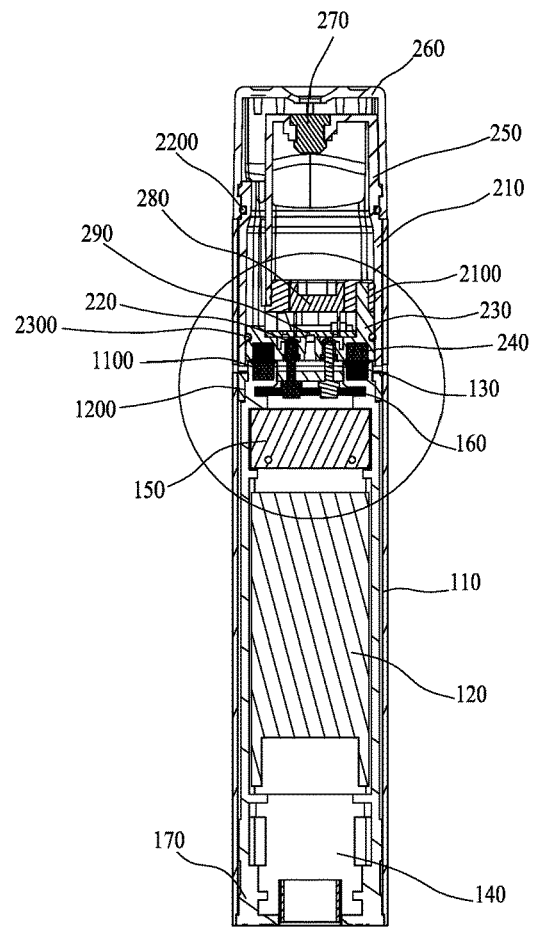
FIG. 4 is a schematic sectional view of the atomizer shown in FIG. 1 according to an embodiment of the disclosure.

Further, as shown in FIG. 4, the battery rod 100 also includes a main control board 140, a switch board 150 and a control circuit 160. The main control board 140, the switch board 150 and the control circuit 160 are all contained in the rod body 110. Optionally, at least two of the main control board 140, the switch board 150 and the control circuit 160 are integrated into one piece. For example, in some embodiments, the main control board 140, the switch board 150 and the control circuit 160 are integrated in a same PCB (also referred to as circuit board); in some embodiments, the main control board 140 and the switch board 150 are integrated on a same PCB, the control circuit 160 is separately provided; in some embodiments, the main control board 140 and the control circuit 160 are integrated on a same PCB, and the switch board 150 is separately provided; in some embodiments, the switch board 150 and the control circuit 160 are integrated on a same PCB, and the main control board 140 is separately provided. Optionally, the main control board 140, the switch board 150, and the control circuit 160 are separately provided.

Figure 6:
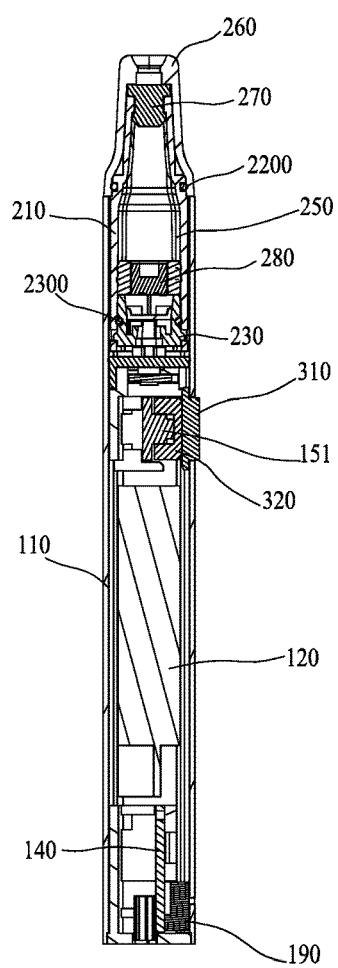
FIG. 6 is a schematic sectional view of the atomizer shown in FIG. 1 taken along another direction according to an embodiment of the disclosure.

In an embodiment of the disclosure, the switch board 150 includes a touch control part 151, and the mechanical switch 300 is cooperative with the touch control part 151, the switch board 150 is configured to obtain a trigger information of the mechanical switch 300. Optionally, as shown in FIG. 6, the mechanical switch 300 includes an operation part 310 and a connection part 320, the connection part 320 is arranged on a side of the operation part 310, the connection part 320 is matched with the touch control part 151 in a concave-convex manner. The concave-convex manner of the connection part 320 and the touch control part 151 can be realized by that the connection part 320 is provided with a groove and the touch control part 151 is provided with a convex, or the connection part 320 is provided with a convex and the touch control part 151 is provided with a groove. It can be understood that the connection part 320 and the touch control part 151 can also be matched in other ways, not limited to the concave-convex manner. Further, a part of the operation part 310 is exposed outside the housing 210, in order to facilitate a user operation. In an exemplary embodiment, the connection part 320 is a flexible structure. For example, a material of the connection part 320 is silicone; of course, the material of the connection part 320 can also be other flexible materials. It can be understood that the structure of the mechanical switch 300 is not limited to the structure of the mechanical switch 300 shown in FIG. 6. For example, the mechanical switch 300 only includes the operation part 310, which is directly matched with the touch control part 151 in the concave-convex manner, or in other matching manners.

In an embodiment of the disclosure, the trigger information includes a first duration of the mechanical switch 300 being triggered and/or a number of times of the mechanical switch 300 being triggered in a preset time period, of course, the trigger information is not limited to this, but can also include other information. Taking the mechanical switch 300 as the push switch, in the embodiment of the disclosure, the mechanical switch 300 is triggered once, that is, the user presses the mechanical switch once. A value of the preset time period is small, and the number of times of the mechanical switch 300 is triggered in the preset time period can be regarded as a continuous operation of the mechanical switch 300. The value of the preset time period can be set as required. For example, the preset time period is 5 seconds; of course, the preset time period can also be set to other numerical values.

Figure 7:
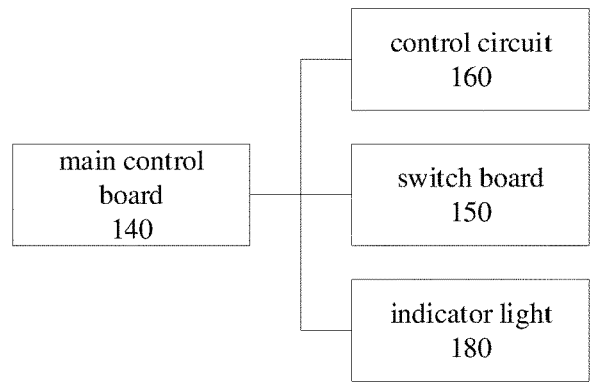
FIG. 7 is a schematic view showing an electrical connection relationship among some of structures of the atomizer according to an embodiment of the disclosure.

The first electrical connection part 130 is electrically connected with the control circuit 160. In addition, as shown in FIG. 7, in an embodiment of the disclosure, the main control board 140 is electrically connected with the battery 120, the switch board 150 and the control circuit 160 individually. In an embodiment of the disclosure, the main control board 140 is capable of controlling the battery rod 100 to be turned on or be turned off according to the trigger information, and after the battery rod 100 is turned on, the main control board 140 is capable of controlling the control circuit 160 whether output a current to the first electrical connection part 130 or not according to the trigger information, and a magnitude and/or a second duration of the current outputted from the control circuit 160, and is further capable of controlling a voltage output rank of the atomizer.

For example, in some embodiments, the trigger information includes the first duration of the mechanical switch 300 being triggered, when the first duration is greater than or equal to a first preset duration, the main control board 140 controls the main control board 140 to output a first current to the first electrical connection part 130, so that the atomizing head 200 performs a heating function, in other words, the mechanical switch 300 is pressed continuously (also referred to as the mechanical switch 300 is pressed for a long time), the main control board 140 controls the control circuit 160 to output the first current to the first electrical connection part 130, so that the atomizing head 200 performs the heating function. Optionally, the first current is an output current of a real-time voltage output rank of the atomizer. The atomizer of the embodiment can include multiple voltage output ranks. For example, the atomizer can include three voltage output ranks: 2.8V output voltage, 3.25V output voltage and 3.6V output voltage. The output currents of different voltage output ranks are different. When the atomizer is used, the atomizer can be set at one of the voltage output ranks to supply a power to the atomizing head 200 through the output current of the voltage output rank. A value of the first preset duration can be set as required. For example, the first preset duration can be 5 seconds or other numerical values.

Furthermore, if the mechanical switch 300 is switched to a non-triggered state, that is, the mechanical switch 300 is released, and the main control board 140 controls the control circuit 160 to stop outputting the first current to the first electrical connection part 130 during the process of the atomizing head 200 performing the heating function, so as to stop the heating function of the atomizing head 200. Optionally, when a second duration of the continuous output current of the control circuit 160 is greater than a second preset duration, the main control board 140 controls the control circuit 160 to stop outputting the first current to the first electrical connection part 130, so as to stop the heating function of the atomizing head 200, that is, after the heating of the atomizing head 200 exceeds a heating time, the heating of the atomizing head 200 is stopped. A value of the second preset duration can be set as required. For example, the second preset duration can be 8 seconds or other.

In some embodiments, the trigger information includes the number of times of the mechanical switch 300 being triggered in the preset time period. When the trigger information indicates that the number of times of the mechanical switch 300 being triggered in the preset time period is a first preset number, the main control board 140 controls the control circuit 160 to output a preheating current to the first electrical connection part 130, so that the atomizing head 200 performs a preheating function, that is, a number of times of continuously operates the mechanical switch 300 is the first preset number, the atomizing head 200 is preheated. Optionally, the preheating default the atomizer is in the voltage output rank of 2.8V output voltage. In this embodiment, the first preset number is greater than or equal to 2, and the first preset number can be set as required. For example, the first preset number can be 2 or other. Furthermore, if the mechanical switch 300 is triggered once (or other times) when the atomizing head 200 performs the preheating function, the main control board 140 controls the control circuit 160 to stop outputting the preheating current to the first electrical connection part 130, so as to stop the preheating function of the atomizing head 200.

In some embodiments, the trigger information includes the number of times of the mechanical switch 300 being triggered in the preset time period. When the trigger information indicates that the number of times of the mechanical switch 300 being triggered in the preset time period is a second preset number, the main control board 140 switches a current voltage output rank to a next voltage output rank. In this embodiment, the second preset number is greater than or equal to 2, and the second preset number can be set according to needs. For example, the second preset number can be 3 times or other. In an exemplary embodiment, a sequence of voltage output rank switching can be 2.8V output voltage→3.25V output voltage→3.6V output voltage, and cycle in turn.

In some embodiments, the trigger information includes the number of times of the mechanical switch 300 being triggered in the preset time period. When the trigger information indicates that the number of times of the mechanical switch 300 being triggered in the preset time period is a third preset number, the main control board 140 controls the battery rod 100 to be turned on or be turned off, and controls the voltage output rank of the atomizer to return to a voltage output rank before the battery rod 100 was turned off. That is to say, when the battery rod 100 is turned off and a number of times of continuous operation of the mechanical switch 300 is the third preset number, the battery rod 100 is turned on, and the voltage output rank of the atomizer is returned to the voltage output rank before the battery rod 100 is turned off; when the battery rod 100 is turned on and the number of times of continuous operation of the mechanical switch 300 is the third preset number, the battery rod 100 is turned off. In this embodiment, the third preset number is greater than or equal to 2, and the third preset number can be set according to the needs, for example, the third preset number can be 5 times or other.

It can be understood that the first preset number, the second preset number and the third preset number are different.

The battery 120 in the embodiment of the disclosure can be a rechargeable battery or a non-rechargeable battery.

For example, in some embodiments, the battery 120 is the rechargeable battery, the battery rod 100 also includes a charging interface arranged on the rod body 110 and exposed outside the rod body 110, the charging interface is electrically connected with the main control board 140, and the charging interface is configured to connect with an external power source. The main control board 140 controls the external power source to charge the battery 120 when the charging interface is connected with the external power source. The charging interface can be arranged at the bottom of the rod body 110 or at other positions of the rod body 110. It should be noted that in the embodiment of the disclosure, during the charging process of the battery 120, the atomizing head 200 cannot be powered through the battery 120.

Refer to FIG. 4 again, the battery rod 100 also includes a mainboard bracket 170, and the main control board 140 is fixed on an inner wall of the rod body 110 through the mainboard bracket 170. In an exemplary embodiment, the main control board 140 can be fixed on the mainboard bracket 170 by means of a snap connection and a threaded connection, and the mainboard bracket 170 can be fixed on the inner wall of the rod body 110 by the snap connection or the threaded connection, etc.

Figure 8:
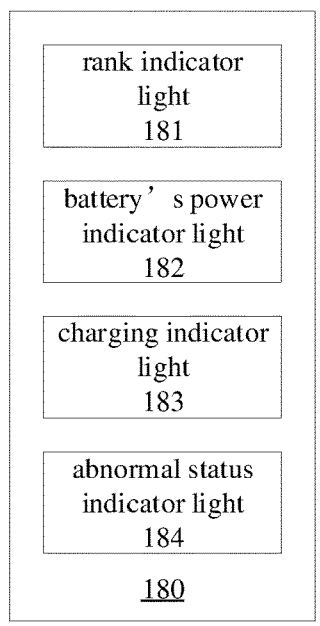
FIG. 8 is a schematic structural view of an indicator light according to an embodiment of the disclosure.
Figure 9:
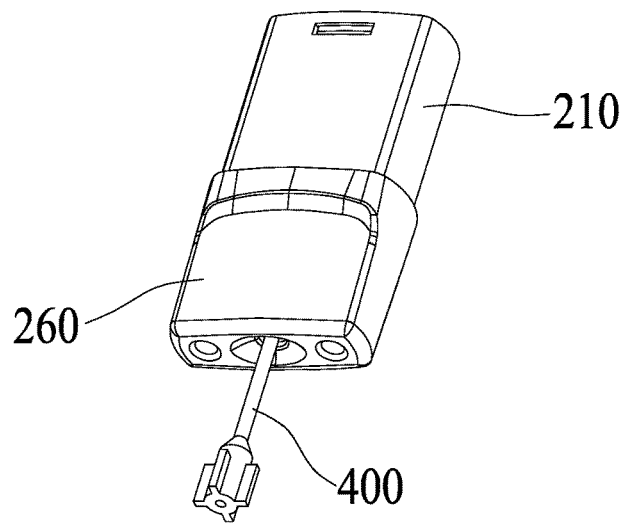
FIG. 9 is a schematic view of a material injection process of an atomizing head according to an embodiment of the disclosure.
Figure 10:
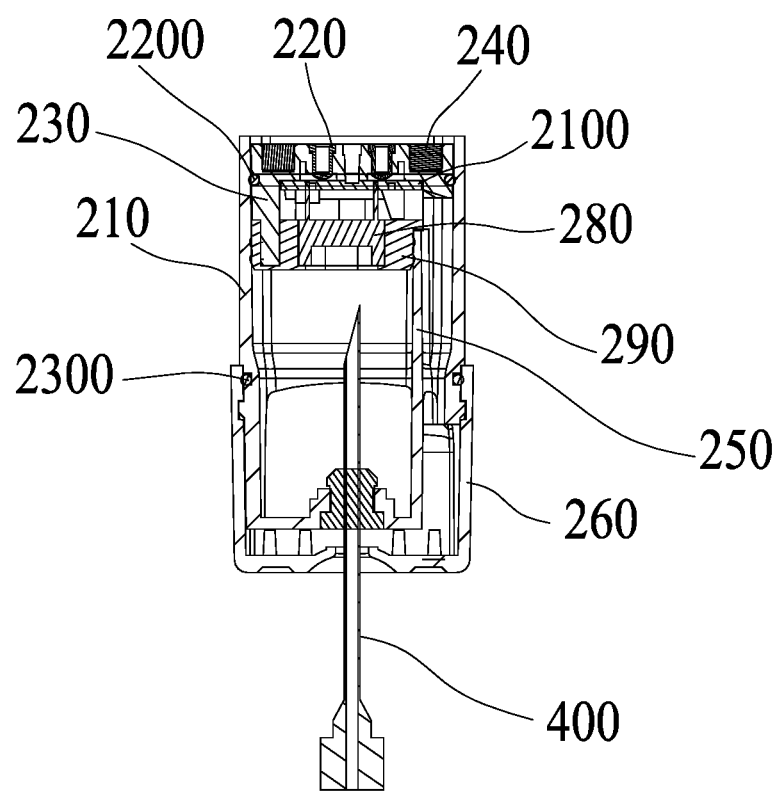
FIG. 10 is a schematic sectional view of the atomizing head shown in FIG. 9 according to an embodiment of the disclosure.

Further, referring to FIG. 7 again, the battery rod 100 also includes an indicator light 180 electrically connected with the main control board 140. The main control board 140 is configured to control a display of the indicator light 180 according to the trigger information to thereby give the user different information. Optionally, referring to FIG. 8, the indicator light 180 includes at least one of a rank indicator light 181, a battery's power indicator light 182, a charging indicator light 183, and an abnormal status indicator light 184. The above-mentioned types of indicator lights 180 are electrical connected to the main control board 140. Of course, the indicator light 180 can also include other types of display lights.

For example, in some embodiments, the atomizer also includes a plurality of rank indicator lights 181, which are electrically connected with the main control board 140, and the plurality of the rank indicator lights 181 are correspond to a plurality of charging voltage ranks of the atomizer. The first current is the current corresponding to one of the charging voltage ranks. When the first duration is greater than or equal to the first preset duration, the main control board 140 turns on a rank indicator light (181) corresponding to the first current to remind the user that the atomizing head 200 enters the heating process. Optionally, when the first duration is greater than or equal to the first preset duration, the main control board 140 controls the rank indicator light 181 corresponding to the first current to change from a first brightness value to a second brightness value, and keeps it on a constant state. The first brightness value is less than the second brightness value, that is, the rank indicator light 181 corresponding to the first current is gradually brighter.

Furthermore, during the process of the heating function of the atomizing head 200, if the mechanical switch 300 is released, the main control board 140 turns off the rank indicator light 181 corresponding to the first current. Optionally, during the heating function of the atomizing head 200, if the mechanical switch 300 is released, the main control board 140 controls the rank indicator light 181 corresponding to the first current to gradually change from a constant on state to an off state, thereby reminding the user that the heating process of the atomizing head 200 is turned off.

Furthermore, when the second duration of the continuous output current of the control circuit 160 is greater than the second preset time, the main control board 140 controls the rank indicator light 181 corresponding to the first current to flash for a fourth preset number, that is, after the heating time-out, the rank indicator light 181 corresponding to the first current flashes for the fourth preset number, thereby reminding the user of the heating timeout of the atomizing head 200. In this embodiment, the fourth preset number can be set according to the needs. For example, the fourth preset number can be 8 times or other.

In some embodiments, the preheating current is the current corresponding to one of the charging voltage ranks. When the trigger information indicates that the number of times of the mechanical switch 300 being triggered in the preset time period is the first preset number, the main control board 140 turns on a rank indicator light 181 corresponding to the preheating current, thus reminding the user that the atomizing head 200 enters the preheating process. Optionally, the main control board 140 turns on the rank indicator light 181 corresponding to the preheating current, which is normally on for 6 seconds or other duration.

In some embodiments, if the mechanical switch 300 is triggered once (or other times) in the process of the atomizing head 200 performing the preheating function, the main control board 140 turns off the rank indicator light 181 corresponding to the preheating current, so as to remind the user that the atomizing head 200 exits the preheating process.

In some embodiments, when the trigger information indicates that the number of times of the mechanical switch 300 being triggered during the preset time period is the second preset number, the main control board 140 also controls a rank indicator light 181 corresponding to the current charging voltage rank to flash for a fifth preset number, moreover, after switching the current charging voltage rank to the next charging voltage rank, the main control board 140 turns on the rank indicator light 181 corresponding to the next charging voltage rank. In this embodiment, the fifth preset number can be set according to needs. For example, the fifth preset number can be 3 times or other.

In some embodiments, when the atomizing head 200 is inserted into the receiving part 111 to cooperate with the atomizing head 200, the main control board 140 turns on a rank indicator light 181 corresponding to the current charging voltage rank of the atomizer to flash for a sixth preset number. In this embodiment, the sixth preset number can be set as required. For example, the sixth preset number can be 3 times or other.

In some embodiments, the atomizer also includes a plurality of battery's power indicator lights 182, which are electrically connected with the main control board 140, each battery's power indicator light 182 displays different colors, and the plurality of the battery's power indicator lights 182 correspond to a plurality of battery levels of the battery 120. When the battery rod 100 is turned on, the main control board 140 can obtain a battery level of the battery 120, and according to the battery level of the battery 120, first control a corresponding battery's power indicator light 182 to flash for a seventh preset number, and then control the corresponding battery's power indicator light 182 to be on normally. In this embodiment, the seventh preset number can be set according to the needs. For example, the seventh preset number can be 5 times or other. For example, the battery's power indicator light 182 includes a blue light, a green light and a red light. When the battery 120 is fully charged, the battery level of the battery 120 is 100%; when the battery level of the battery 120 is greater than or equal to 70%, the blue light is turned on; when the battery level of the battery 120 is greater than or equal to 30% and less than 70%, the green light is turned on; when the battery level of the battery 120 is less than 30%, the red light is turned on.

In some embodiments, the atomizer also includes a charging indicator light 183, which is electrically connected with the main control board 140. In the process of charging the battery 120 by the external power source, the main control board 140 controls the charging indicator light 183 to be always on and displays a first color; when the battery level of the battery 120 is greater than a preset full charging amount, the main control board 140 controls the charging indicator light 183 to flash for an eighth preset number and display a second color. The first color and the second color can be set as needed. For example, the first color is red and the second color is blue. In this embodiment, the eighth preset number can be set according to needs, for example, the eighth preset number can be 20 times, or other times.

In some embodiments, the atomizer also includes an abnormal status indicator light 184, which is electrically connected with the main control board 140. When the voltage of the battery 120 is less than a preset voltage, the main control board 140 can control the battery 120 to enter the low-voltage protection state, and control the abnormal status indicator light 184 to flash for a ninth preset number. In this way, the low-voltage protection prompt can be given to the user; when there is an abnormal short-circuit in the battery rod 100, the main control board 140 can control the battery rod 100 to enter the short-circuit protection state, and control the abnormal status indicator light 184 to flash for a tenth preset number. In this way, the user can be prompted for short-circuit protection. In this embodiment, the ninth preset number can be set according to the needs. For example, the ninth preset number can be 10 times or other. The tenth preset number can also be set as required. For example, the tenth preset number can be 3 times or other. The abnormal status indicator light 184 can be a display light that outputs white light.

The indicator light 180 can be arranged on the main control board 140, the switch board 150 and/or the control circuit 160. The light emitted by the indicator light 180 of the embodiment of the disclosure can be emitted out of the rod body 110 for display to the user.

Referring to FIG. 6 again, the battery rod 100 may also include a shading structure 190, and a light emitted from the indicator light 180 is directed outside the rod body 110 after passing through the shading structure 190, and the light emitted from the indicator light 180 can be dispersed to make the light softer. Optionally, the shading structure 190 is a flexible structure, and the material of the shading structure 190 is silicone; of course, the material of the shading structure 190 can also be other flexible materials.

The indicator light 180 can be an LED light or other type of display light.

In an embodiment of the disclosure, the first electrical connection part 130 is matched with the second electrical connection part 220, optionally, the first electrical connection part 130 is one of an electric pin and an electric socket, and the second electrical connection part 220 is the other of the electric pin and the electric socket; Of course, the first electrical connection part 130 and the second electrical connection part 220 can also be designed as other structures. For example, the first electrical connection part 130 and the second electrical connection part 220 are matched female head and male head.

Figure 5:
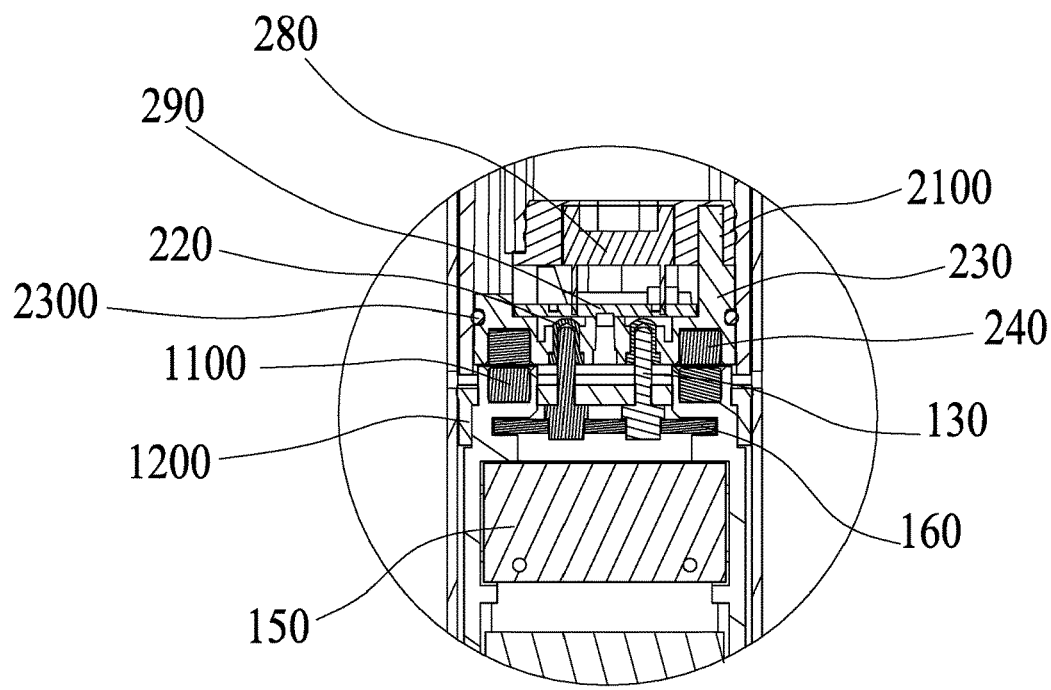
FIG. 5 is a schematic partially enlarged view of the atomizer shown in FIG. 4 according to an embodiment of the disclosure.

For example, please refer to FIG. 5. In some embodiments, the first electrical connection part 130 is the electric pin and the second electrical connection part 220 is the electrical socket. Optionally, the first electrical connection part 130 includes two electric pins, the second electrical connection part 220 includes two electric sockets, and the two electric pins are matched with the two electrical sockets.

Furthermore, the battery rod 100 can also include first magnetic parts 1100 arranged on the rod body 110 and on two sides of the first electrical connection part 130, and the first magnetic part 1100 is located in the receiving part 111. The atomizing head 200 may also include second magnetic parts 240 arranged on the housing 210 and on two sides of the second electrical connection part 220. The first magnetic parts 1100 are magnetically connected with the second magnetic parts 240 to fix the atomizing head 200 on the battery rod 100 when the atomizing head 200 is inserted into the receiving part 111. The connection manner of the atomizing head 200 and the battery rod 100 adopts a magnet in-line thimble matching structure, which is different from the existing spring electrode contact manner. This structure effectively avoids the failure of the existing spring electrode due to the high heat generated during the operation of the atomizer, resulting in poor contact of the atomizing head 200 and the like.

Furthermore, the battery rod 100 can also include a flexible sheath 1200, which is arranged at an end of the housing 210 and contained in the receiving part 111. When the atomizing head 200 is inserted into the receiving part 111, the atomizing head 200 contacts with the flexible sheath 1200, and an impact force during the connection between the atomizing head 200 and the battery rod 100 is buffered by the flexible sheath 1200. The material of the flexible sheath 1200 can be silicone or other flexible materials.

Furthermore, please refer to FIG. 4 and FIG. 5, the atomizing head 200 may also include a first block 230 contained in the housing 210, and the second electrical connection part 220 and the second magnetic parts 240 are fixed on the first block 230. Optionally, the second electrical connection part 220 and the second magnetic parts 240 are embedded on the first block 230, and the first block 230 is fixedly connected with the inner wall of the housing 210.

Please refer to FIG. 4, FIG. 6, FIG. 7, and FIG. 8, the atomizing head 200 can also include a material-receiving cup 250 contained in the housing 210 and an atomizing nozzle 260 sleeved on the housing 210 and exposed outside, a gap is arranged to a top of the material-receiving cup 250, which is directly opposite to the atomizing nozzle 260, and the gap is sealed by a sealing plug 270. When the sealing plug 270 is removed from the gap, the gap is connected with the nozzle hole on atomizing nozzle 260.

In an exemplary embodiment, an needle 400 located outside of the atomizer passes through the sealing plug 270 from the atomizing nozzle 260 and enters the material-receiving cup 250 to inject materials when the atomizing head 200 is inverted; the sealing plug 270 is restored automatically under an action of a surrounding pressure to seal the gap after the needle 400 is pulled out. It should be noted that when the atomizing head 200 is inverted, the receiving part 111 is upward and the atomizing nozzle 260 is downward. The atomizing head 200 adopts an inverted material injection mode. Specifically, the atomizing nozzle 260 is downward and inverted for 90 degrees; the needle 400 pierces the sealing plug 270 from the middle of hole of the atomizing nozzle 260 and injects the materials to the material-receiving cup 250. After the injection, the needle 400 is pulled out, and the sealing plug 270 is automatically restored by the surrounding pressure to play a sealing role. In this way, the materials will not directly arrive at the lower material hole during the feeding process, thus avoiding the risk of material leakage in the injection process. The material of the embodiment can be liquid or granular, and the material is a combustible material. It should be noted that the needle 400 can be the needle of the syringe or the needle matched with the injection machine.

In an exemplary embodiment, the material of the sealing plug 270 can be silicone or other materials.

Please refer to FIG. 4 to FIG. 6 and FIG. 8, the atomizing head 200 of an embodiment of the disclosure can also include a heating element 280, which can be arranged under the material-receiving cup 250 to heat the materials in the material-receiving cup 250, so as to make the materials heated and atomized. Further, the atomizing head 200 may include a control board which is electrically connected with the second electrical connection part 220 and the heating element 280 individually. When the electric connection between the first electrical connection part 130 and the second electrical connection part 220 is turned on, the atomizing head 200 is powered on, and the control board can control the heating or preheating of the heating element 280, and the heating power or preheating power of the heating element 280 is related to the output current of the first electrical connection part 130.

Optionally, the heating element 280 is made of a ceramic material; of course, the heating element 280 can also be made of other materials for heating. Furthermore, the heating element 280 is an interior-type lead-free ceramic heater (also referred to as buried lead-free ceramic heater), which can make the gas generated after atomization reach a higher reduction degree and make the product more environmentally friendly, safe and healthy.

In an embodiment of the disclosure, when the atomizing head 200 is placed upright, the heating element 280 is arranged between the bottom of the material-receiving cup 250 and the second electrical connection part 220.

Referring to FIG. 4 and FIG. 5 again, the atomizing head 200 may also include a second block 290 and a flexible part 2100, both of which are contained in the housing 210. In an exemplary embodiment, the second block 290 is arranged between the bottom of the heating element 280 and the second electrical connection part 220, and the second block 290 is fixed on the first block 230. The heating element 280 is wrapped in the flexible part 2100; the flexible part 2100 is fixed on the first block 230.

The second block 290 may be a flexible material, such as silicone or other materials. In addition, the material of the flexible part 2100 can be silicone or other materials.

As shown in FIG. 4, a first flexible ring 2200 is also arranged at the joint of atomizing nozzle 260 and the housing 210, so as to make the atomizing nozzle 260 and the housing 210 more tightly sealed. In an exemplary embodiment, the first flexible ring 2200 can be a silicone rubber ring or a sealing ring made of other flexible materials.

Further, referring to FIG. 6, a second flexible ring 2300 is also arranged at the joint between the first block 230 and the inner wall of the housing 210, so that the sealing between the first block 230 and the inner wall of the housing 210 is better. In an exemplary embodiment, the second flexible ring 2300 can be a silicone rubber ring or a sealing ring made of other flexible materials.

Finally, it should be noted that the foregoing description merely illustrates some embodiments of the invention, and is not intended to limit the scope of the invention. Although the invention has been disclosed in the above embodiments, it is not intended to limit the invention. Any person skilled in the art can make some amendments or modifications as equivalent embodiments according to the above disclosed technical contents without departing from the technical scope of the invention. As long as they are without departing from the technical scope of the invention, any simple amendments, equivalent changes and modifications to the above embodiments according to the technical essence of the disclosure are still within the technical scope of the invention.

What is claimed is:

1. An atomizer, comprising:
a battery rod (100), comprising a rod body (110), a battery (120) contained in the rod body (110), and a first electrical connection part (130) arranged on the rod body (110) and exposed from the rod body (110), wherein an end of the rod body (110) is disposed with a receiving part (111), and the first electrical connection part (130) is located in the receiving part (111);
an atomizing head (200), comprising a housing (210) and a second electrical connection part (220) arranged on the housing (210) and exposed from the housing (210);
a mechanical switch (300), arranged on the rod body (110) and exposed outside the rod body (110), wherein the mechanical switch (300) is electrically connected between the battery (120) and the first electrical connection part (130), and configured to turn on or turn off an electrical connection between the battery (120) and the first electrical connection part (130);
wherein the first electrical connection part (130) is in contact with the second electrical connection part (220) when the atomizing head (200) is inserted into the receiving part (111);
wherein the electrical connection between the battery (120) and the first electrical connection part (130) is turned on when the atomizing head (200) is inserted into the receiving part (111) and the mechanical switch (300) is triggered, and thereby an electrical connection between the first electrical connection part (130) and the second electrical connection part (220) is turned on to supply a power to the atomizing head (200) through the battery (120);
wherein the battery rod further comprises: first magnetic parts (1100); the receiving part (111) comprises a first plate connected to the rod body (110), the first electrical connection part (130) penetrates through the first plate and extends out the first plate, and the first magnetic parts (1100) are arranged on the first plate and on two sides of the first electrical connection part (130); the atomizing head (200) further comprises: a second plate and second magnetic parts (240) corresponding to the first magnetic parts (1100), the second plate is provided with a first hole and second holes, the first hole corresponds to the second electrical connection part (220), and the second holes correspond to the second magnetic parts (240), respectively;
when the atomizing head (200) is inserted into the receiving part (111), the housing (210) of the atomizing head (200) is disposed in the receiving part (111), an extending part of the first electrical connection part (130) passes through the first hole to be in contact with the second electrical connection part (220), the first magnetic parts (1100) pass through the second holes to be magnetically connected with the second magnetic parts (240), thereby to make the first plate be in contact with the second plate, and a projection of each first magnetic part (1100) on the first plate and a projection of the corresponding second magnetic part (240) on the second plate at least partially overlap.

2. The atomizer as claimed in claim 1, wherein the battery rod (100) further comprises a main control board (140), a switch board (150) and a control circuit (160); the main control board (140), the switch board (150) and the control circuit (160) are all contained in the rod body (110);
wherein the switch board (150) comprises a touch control part (151), and the mechanical switch (300) is cooperative with the touch control part (151); the switch board (150) is configured to obtain a trigger information of the mechanical switch (300), and the trigger information comprises a first duration of the mechanical switch (300) being triggered and/or a number of times of the mechanical switch (300) being triggered in a preset time period;
wherein the first electrical connection part (130) is electrically connected with the control circuit (160);
wherein the main control board (140) is electrically connected with the battery (120), the switch board (150) and the control circuit (160) individually, the main control board (140) is capable of controlling the battery rod (100) to be turned on or be turned off according to the trigger information; and after the battery rod (100) is turned on, the main control board (140) is capable of controlling the control circuit (160) to whether output a current to the first electrical connection part (130) or not according to the trigger information, and a magnitude and/or a second duration of the current outputted from the control circuit (160), and is further capable of controlling a voltage output rank of the atomizer.

3. The atomizer as claimed in claim 2, wherein the mechanical switch (300) comprises an operation part (310) and a connection part (320), the connection part (320) is arranged on a side of the operation part (310), the connection part (320) is matched with the touch control part (151) in a concave-convex manner, a part of the operation part (310) is exposed outside the housing (210), and the connection part (320) is a flexible structure; and/or,
at least two of the main control board (140), the switch board (150) and the control circuit (160) are integrated into one piece.

4. The atomizer as claimed in claim 2, wherein the battery rod (100) further comprises a charging interface arranged on the rod body (110) and exposed outside the rod body (110), the charging interface is electrically connected with the main control board (140), and the charging interface is configured to connect with an external power source;
wherein the main control board (140) controls the external power source to charge the battery (120) when the charging interface is connected with the external power source.

5. The atomizer as claimed in claim 2, wherein the battery rod (100) further comprises an indicator light (180) electrically connected with the main control board (140), and the main control board (140) is configured to control a display of the indicator light (180) according to the trigger information.

6. The atomizer as claimed in claim 3, wherein the battery rod (100) further comprises an indicator light (180) electrically connected with the main control board (140), and the main control board (140) is configured to control a display of the indicator light (180) according to the trigger information.

7. The atomizer as claimed in claim 4, wherein the battery rod (100) further comprises an indicator light (180) electrically connected with the main control board (140), and the main control board (140) is configured to control a display of the indicator light (180) according to the trigger information.

8. The atomizer as claimed in claim 5, wherein the indicator light (180) comprises at least one of a rank indicator light (181), a battery's power indicator light (182), a charging indicator light (183) and an abnormal status indicator light (184); and/or,
wherein the battery rod (100) further comprises a shading structure (190), and a light emitted from the indicator light (180) is directed outside the rod body (110) after passing through the shading structure (190); and/or,
wherein the shading structure (190) is a flexible structure.

9. The atomizer as claimed in claim 6, wherein the indicator light (180) comprises at least one of a rank indicator light (181), a battery's power indicator light (182), a charging indicator light (183) and an abnormal status indicator light (184); and/or,
wherein the battery rod (100) further comprises a shading structure (190), and a light emitted by the indicator light (180) is directed outside the rod body (110) after passing through the shading structure (190); and/or,
wherein the shading structure (190) is a flexible structure.

10. The atomizer as claimed in claim 7, wherein the indicator light (180) comprises at least one of a rank indicator light (181), a battery's power indicator light (182), a charging indicator light (183) and an abnormal status indicator light (184); and/or,
wherein the battery rod (100) further comprises a shading structure (190), and a light emitted by the indicator light (180) is directed outside the rod body (110) after passing through the shading structure (190); and/or,
wherein the shading structure (190) is a flexible structure.

11. The atomizer as claimed in claim 1, wherein the first electrical connection part (130) is one of an electric pin and an electric socket, and the second electrical connection part (220) is the other of the electric pin and the electric socket; and/or,
wherein the first electrical connection part (130) comprises two electric pins, the second electrical connection part (220) comprises two electric sockets, and the two electric pins are matched with the two electric sockets.

12. The atomizer as claimed in claim 1, wherein the atomizing head (200) further comprises a material-receiving cup (250) contained in the housing (210) and an atomizing nozzle (260) sleeved on the housing (210) and exposed outside;
wherein a gap is arranged on a top of the material-receiving cup, and the gap is sealed by a sealing plug (270);
wherein a needle (400) located outside of the atomizer passes through the sealing plug (270) from the atomizing nozzle (260) and enters into the material-receiving cup (250) to inject materials when the atomizing head (200) is inverted;
wherein the sealing plug (270) is restored automatically under an action of a surrounding pressure to seal the gap after the needle (400) is pulled out.

13. The atomizer as claimed in claim 12, wherein the atomizing head (200) further comprises a heating element (280), the heating element (280) is arranged under the material-receiving cup (250), and the heating element (280) is made of a ceramic material; and/or,
wherein the heating element (280) is an interior-type lead-free ceramic heater.

14. The atomizer as claimed in claim 13, wherein the atomizing head (200) further comprises:
a first block (230), connected to the housing (210); wherein the first block (230) is provided with a first groove corresponding to the first hole and second grooves corresponding to the second holes, the second electrical connection part (220) is disposed in the first groove and fixed on the first block (230), and the second magnetic parts (240) are disposed in the second grooves and fixed on the first block (230); and
a flexible part (2100), fixed on the first block (230); wherein the heating element (280) is wrapped in the flexible part (2100).

15. The atomizer as claimed in claim 14, wherein the housing (210) is provided with a first circular groove, and an opening of the first circular groove faces toward the atomizing nozzle (260); and the first block (230) is provided with a second circular groove, and an opening of the second circular groove faces towards the housing (210); and the atomizing head (200) further comprises: a first flexible ring (2200) disposed in the first circular groove and between the atomizing nozzle (260) and the housing (210), and a second flexible ring (2300) disposed in the second circular groove and between the first block (230) and an inner wall of the housing (210).

16. The atomizer as claimed in claim 14, wherein the atomizing head (200) further comprises: a second block (290) arranged between a bottom of the heating element (280) and the second electrical connection part (220), the second block (290) is fixed on the first block (230), the heating element (280) is provided with extending portions, and the extending portions penetrate into the second block (290).

17. The atomizer as claimed in claim 2, wherein the battery rod (100) further comprises: a mainboard bracket (170) and a flexible sheath (1200);
the mainboard bracket (170) is disposed in the rod body (110) and provided with longitudinal grooves, a first transverse groove disposed below the longitudinal grooves, a second transverse groove adjacent to the first transverse groove, a third transverse groove adjacent to the second transverse groove and a fourth transverse groove adjacent to the third transverse groove; and the first magnetic parts (1100) are disposed in the longitudinal grooves respectively, the control circuit (160) is disposed in the first transverse groove, the switch board (150) is disposed in the second transverse groove, the battery (120) is disposed in the third transverse groove, and the main control board (140) is disposed in the fourth transverse groove;
the flexible sheath (1200) is disposed in the receiving part (111), and when the atomizing head (200) is inserted into the receiving part (111), the flexible sheath (1200) is in contact with the housing (210).

18. An atomizer, comprising: a battery rod (100), comprising: a rod body (110); a battery (120) contained in the rod body (110); electric pins, arranged on the rod body (110); first magnetic parts (1100) arranged on the rod body (110); wherein an end of the rod body (110) is disposed with a receiving part (111), and the electric pins and the first magnetic parts (1100) are located in the receiving part (111) and spaced apart from one another; the receiving part (111)

comprises a first plate connected to the rod body (110), the electric pins penetrate through the first plate and extends out the first plate, and the first magnetic parts (1100) are arranged on the first plate and on two sides of the electric pins; an atomizing head (200), comprising: a housing (210); electric sockets arranged on the housing (210); second magnetic parts (240) arranged on the housing (210); a material-receiving cup (250) contained in the housing (210); an atomizing nozzle (260) sleeved on the housing (210) and exposed outside; a first block (230), connected to the housing (210); wherein the first block (230) is provided with first grooves and second grooves, the electric sockets are disposed in the first grooves and fixed on the first block (230), and the second magnetic parts (240) are disposed in the second grooves and fixed on the first block (230); a flexible part (2100), fixed on the first block (230); and a heating element (280) arranged under the material-receiving cup (250) and wrapped in the flexible part (2100); the atomizing head (200) further comprises: a second plate, the second plate is provided with a first hole and second holes, the first hole corresponds to the electric sockets, and the second holes correspond to the second magnetic parts (240), respectively; a mechanical switch (300), arranged on the rod body (110) and exposed outside the rod body (110); wherein the mechanical switch (300) is electrically connected between the battery (120) and the electric pins, when the atomizing head (200) is inserted into the receiving part (111), the housing (210) of the atomizing head (200) is disposed in the receiving part (111), the electric pins are in contact with the electric sockets, the first magnetic parts (1100) are magnetically connected with the second magnetic parts (240), and a projection of each of the first magnetic parts (1100) on the corresponding second magnetic part (240) at least partially cover the corresponding second magnetic part (240).

19. The atomizer according to claim 18, wherein the housing (210) is provided with a first circular groove, and an opening of the first circular groove faces toward the atomizing nozzle (260); and the first block (230) is provided with a second circular groove, and an opening of the second circular groove faces towards the housing (210); the atomizing head (200) further comprises:
- a first flexible ring (2200) disposed in the first circular groove and between the atomizing nozzle (260) and the housing (210);
- a second flexible ring (2300) disposed in the second circular groove and between the first block (230) and an inner wall of the housing (210);
- a second block (290) arranged between a bottom of the heating element (280) and the second electrical connection part (220), wherein the second block (290) is fixed on the first block (230), the heating element is provided with extending portions, and the extending portions penetrate into the second block (290).

20. The atomizer according to claim 19, wherein the battery rod (100) further comprises: a mainboard bracket (170) disposed in the rod body (110), and the mainboard bracket (170) is provided with longitudinal grooves, a first transverse groove disposed below the longitudinal grooves, a second transverse groove adjacent to the first transverse groove, a third transverse groove adjacent to the second transverse groove and a fourth transverse groove adjacent to the third transverse groove; and the first magnetic parts (1100) are disposed in the longitudinal grooves respectively, the control circuit (160) is disposed in the first transverse groove, the switch board (150) is disposed in the second transverse groove, the battery (120) is disposed in the third transverse groove, and the main control board (140) is disposed in the fourth transverse groove; and
- wherein the battery rod (100) further comprises: a flexible sheath (1200) disposed in the receiving part (111), and when the atomizing head (200) is inserted into the receiving part (111), the flexible sheath (1200) is in contact with the housing (210).

\* \* \* \* \*